United States Patent
Zhao et al.

(10) Patent No.: US 6,689,713 B1
(45) Date of Patent: Feb. 10, 2004

(54) COPPER-CONTAINING CATALYST AND A PROCESS FOR THE PREPARATION THEREOF

(75) Inventors: Leiping Zhao, Fushun (CN); Lijuan Zhang, Fushun (CN); Yuzhuo Chen, Fushun (CN); Yuliang Wang, Fushun (CN)

(73) Assignees: China Petrochemical Corporation (CN); Fushun Research Institute of Petroleum and Petrochemicals, Sinopec (CN)

(*) Notice: Subject to any disclaimer, the term of this patent is extended or adjusted under 35 U.S.C. 154(b) by 0 days.

(21) Appl. No.: 09/439,928

(22) Filed: Nov. 12, 1999

(30) Foreign Application Priority Data

Nov. 16, 1998 (CN) .......................... 98121080 A
Sep. 29, 1999 (CN) .......................... 99113288 A

(51) Int. Cl.⁷ ............................... B01J 23/72
(52) U.S. Cl. ..................................... 502/345
(58) Field of Search ................ 502/342, 343, 502/345, 346, 355; 423/42, 43, 593

(56) References Cited

U.S. PATENT DOCUMENTS

| | | | | |
|---|---|---|---|---|
| 5,155,086 A | * | 10/1992 | Thakur et al. | 502/342 |
| 5,897,958 A | * | 4/1999 | Yamada et al. | 446/474 |
| 6,054,497 A | * | 4/2000 | Sofianos et al. | 518/713 |
| 6,060,026 A | * | 5/2000 | Goldstein | 422/186 |
| 6,124,234 A | * | 9/2000 | Fetzer et al. | 502/326 |
| 6,200,680 B1 | * | 3/2001 | Takeda et al. | 428/402 |

FOREIGN PATENT DOCUMENTS

| | | | | |
|---|---|---|---|---|
| DE | WO-97/03937 A1 | * | 2/1997 | C07C/29/154 |
| JP | WO-95/33688 A1 | * | 12/1995 | C01G/9/02 |
| SU | B-829621 | | 5/1947 | |
| SU | A-582829 | | 12/1977 | |
| SU | 709163 A | | 1/1980 | |
| SU | B-736998 | | 5/1980 | |
| WO | WO95/33688 | | 12/1995 | |

OTHER PUBLICATIONS

XP–000901598, Catalysis Today, 2 (1988) 643–652 No Month.

* cited by examiner

*Primary Examiner*—Steven P. Griffin
*Assistant Examiner*—Edward M. Johnson
(74) *Attorney, Agent, or Firm*—Anderson Kill & Olick, P.C.

(57) ABSTRACT

This invention relates to a copper-containing catalyst, a process for the preparation thereof and uses of the catalyst. The catalyst includes copper oxide of 30–70 wt %, zinc oxide of 30–70 wt %, alumina of 0–30 wt % and no sodium, and has a specific surface area of 30–50 $m^2/g$, a pore volume of 0.10–0.25 ml/g, and an average pore diameter of 10–25 nm and has a uniform crystallite distribution wherein the crystallites having a diameter of less than 1.0 nm account for 0–10%, thoseof 1.0–2.0 nm account for 80–95%, and those of more than 2.0 nm account for 0–10%. The process includes a co-precipitation method using an organic acid and/or an ammonium salt thereof as precipitant to provide a copper-containing catalyst having a relatively large specific surface area and pore volume, and a uniform crystallite distribution.

26 Claims, 1 Drawing Sheet

COPPER-CONTAINING CATALYST AND A PROCESS FOR THE PREPARATION THEREOF

FIELD OF THE INVENTION

The present invention relates to a copper-containing catalyst, a process for the preparation thereof and uses of the same.

BACKGROUND OF THE INVENTION

Copper-containing catalysts, for example, catalysts containing copper and zinc oxide or catalysts containing copper, zinc oxide and alumina, have been used widely in industries as conventional catalysts in many processes such as low temperature transformation, methanol synthesis, hydro/dehydrogenation processes and so on.

Copper-containing catalysts are generally prepared by a coprecipitation method, that is, by adding a basic coprecipitant, for example, an alkali metal salt such as sodium carbonate, sodium bicarbonate and ammonium carbonate, to a mixed solution of a soluble copper salt, zinc salt and aluminum salt to precipitate out copper, zinc and aluminum as insoluble subcarbonates, which is then filtered, washed, dried, calcined, and pressed and moulded into a catalyst. EP 125,689 discloses a process for preparing a copper-containing catalyst used in methanol synthesis process, wherein the catalyst has an atomic ratio of copper to zinc of 2.8–3.8 (corresponding to 26.9–36.5 parts of zinc oxide per 100 parts of copper oxide), and the parts of alumina is 8–12. In the preparation process, copper and zinc are introduced into the catalyst by a coprecipitation method by adding such a precipitant as sodium carbonate to a solution of the metal salts, and alumina is introduced in the form of aluminum hydroxide sol into the catalyst. U.S. Pat. No. 4,876,402 discloses a process for preparing a catalyst containing copper and zinc oxide for the hydrogenation of aldehydes in gas phase by using sodium carbonate as coprecipitant. In the preparation process of the catalyst the resultant precipitate needs to be pulped, washed and filtered for 4 times in order to remove the sodium salt from the coprecipitate. Nevertherness, as admitted in the prior arts including U.S. Pat. No. 3,303,001 have recognized, copper oxide/zinc oxide catalysts prepared by the standard coprecipitation technique of the prior art will still contain a small amount of sodium. However, the presence of sodium in the catalysts is undesirable because alkali metals, in particular sodium, will diminish the activity of the catalysts. In addition, in the prior arts, copper-containing catalysts are prepared by a coprecipitation method with a basic substance, especially, sodium carbonate, as coprecipitant. Such a preparation process is carried out under a basic condition and zinc compound was precipitates first followed by copper compound, thus it is liable to form inhomogeneous coprecipitates, resulting in non-uniform catalyst crystallite sizes (1.0–10 nm) in irregular crystal shapes, of which the larger crystallites are 10 times the size of the smaller. In order to obtain catalysts of excellent activity and stability, the crystallites of copper oxide should be evenly separated by zinc oxide, but this cannot be achieved by the sodium carbonate method of the prior art. Another disadvantage of using sodium carbonate as coprecipitant is that, since the resulting coprecipitate shall be pulped, washed and filtered repeatedly to remove the undesired sodium salt, it consumes large amounts of pure water and as a result, a large quantity of waste water is discharged and needs to be treated or otherwise will pollute the environment, so the complexity of preparation and the production costs of the catalyst are further increased. The last point, but not least in importance, to be mentioned is that, the specific surface area of the catalysts prepared according to the prior art process is not large enough, and the pore volume and bulk specific weight are all relatively low, so, with respect to the catalytic performance, the catalysts exhibit unsatisfactory activity and selectivity and poor stability.

Therefore, there is a need in the art to develop a copper-containing catalyst having uniform crystallite distribution, large specific surface area and pore volume and, high activity and good stability, and a process for the preparation thereof.

After extensive studies and experiments, the inventors have discovered a novel process comprising a coprecipitation method for the preparation of a copper-containing catalyst featuring a uniform crystallite distribution and showing excellent catalytic performances.

SUMMARY OF THE INVENTION

An object of the invention is to provide a copper-containing catalyst featuring a uniform crystallite distribution and showing excellent catalytic performances.

Another object of the invention is to provide a process for preparing a copper-containing catalyst by a coprecipitation method, comprising the step of mixing a working solution containing soluble metal salts for coprecipitation and a solution containing organic acid(s) and/or ammonium salt(s) thereof as coprecipitant to coprecipitate out a mixture of insoluble metal salts containing copper. Said process has overcome the problems of environmental protection existing in the prior art, while the costs for production and starting materials are reduced.

A further object of the invention is to provide a use of the copper-containing catalyst according to the present invention in various chemical processes in which the catalytic action of a copper-containing catalyst is needed, including hydrogenation of aldehydes and/or ketones in gas phase, dehydrogenation of alcohols in gas phase, and a process of methanol synthesis from a mixed gas of CO, $CO_2$ and $H_2$.

These and other objects of the invention will become apparent to the person skilled in the art after reading the specification.

DETAILED DESCRIPTION OF THE INVENTION

The copper-containing catalyst of the present invention is prepared by a novel process comprising a coprecipitation method and has a uniform crystallite distribution wherein the crystallites having a diameter of less than 1.0 nm account for 0–20%, preferably 0–15%, more preferably 0–10% and most preferably 2–5%; those of 1.0–2.0 nm account for 70–99%, preferably 75–98%, more preferably 80–95% and most preferably 85–90%; and those of more than 2.0 nm account for 0–20%, preferably 0–15%, more preferably 0–10% and most preferably 2–5%.

The copper-containing catalyst of the present invention comprises copper oxide of 30–70 wt %, preferably 33–50 wt %; zinc oxide of 30–70 wt %, preferably 50–65 wt %; and alumina of 0–30 wt %, preferably 10–25 wt % based on the weight of the catalyst.

The copper-containing catalyst of the present invention has a specific surface area of 30–50 $m^2/g$, preferably 35–45 $m^2/g$; a pore volume of 0.10–0.25 ml/g, preferably 0.15–0.20 ml/g; and an average pore diameter of 15–20 nm.

Since sodium salt is not used as a precipitant in the preparation process, sodium can be avoided being introduced into the catalyst. The copper-containing catalyst of the present invention preferably contains no sodium.

The process for preparing the catalyst according to the present invention comprises the steps of:

mixing a working solution containing soluble metal salts for coprecipitation and a solution containing organic acid(s) and/or ammonium salt(s) thereof as coprecipitant to coprecipitate out a mixture of insoluble metal salts; aging and filtering the mixture to obtain a filter cake, drying and calcining to form mixed oxides of catalyst, and then pressing and moulding the mixture to obtain the catalyst which can be in any suitable shape, such as tablet, cylindrical, bar, spherical and the like.

Said soluble metal salts are copper salt(s) and the salt(s) of other metal(s) used as essential metal components of the catalyst, which can be, for example, either copper salt(s), zinc salt(s) and aluminum salt(s), or copper salt(s) and zinc salt(s), selected from the group consisting of chlorides, sulfates, nitrates and acetates. Said organic acid(s) as coprecipitant can be one or more soluble organic acid(s) and may be selected from the group consisting of oxalic acid, malonic acid, succinic acid, and glutaric acid and ammonium salts thereof, preferably malonic acid, oxalic acid and ammonium salts thereof.

The coprecipitation process of the metal salts comprises:

preparing a working salt solution for coprecipitation using the metal salts as starting materials, having a specific concentration of 0.10–0.80M, preferably 0.30–0.50M;

preparing a coprecipitant solution using organic acid(s) and/or ammonium salt(s) thereof as starting material, having a specific concentration of 0.1–0.8M, preferably 0.3–0.5M, and a pH value of 3.0–7.0, preferably 4.0–6.0; wherein the amount of said coprecipitant used in the coprecipitation process exceeds by 5–20 wt %, preferably by 10–15 wt % over the stoichiometrical amount of the metal ions completely precipitated from the working salt solution;

mixing and coprecipitating the above two solutions at a temperature of 15–70° C., preferably 25–45° C. with stirring and heat preservation to obtain a coprecipitate in suspension; and aging under a heat preservation condition, filtering and drying in natural air and so on to obtain a coprecipitate filter cake.

The coprecipitation process mentioned above may be conducted by adding the working salt solution to the precipitant solution, or vice versa, or by heating them separately and adding them simultaneously into a precipitation tank.

The precipitation process mentioned above may be carried out by adding the working salt solution and the precipitant solution separately but simultaneously into two parallel elevated tanks, heating respectively to 15–70° C., preferably 25–45° C., and then adding them simultaneously into a precipitation tank at a lower position with stirring and heat preservation.

The catalyst of the present invention can be prepared by drying and calcining the coprecipitate filter cake obtained above, pressing and moulding the obtained mixture of the oxides optionally together with a given amount of a pressing assistant to obtain the catalyst. The drying is carried out at a temperature of 80–150° C., preferably 100–120° C., for 6–20 hours, preferably for 8–10 hours; the calcination is carried out at a temperature of 300–500° C., preferably 340–370° C., for 2–8 hours, preferably for 4–5 hours; the weight ratio of the pressing assistant to dry substrate is 2.0–5.0 wt %, and said pressing assistant may be graphite and/or stearic acid and the like.

The oxides obtained from the steps of drying and calcining and so on mentioned above may be mixed homogeneously with the pressing assistant and a binder, then pressed and moulded to obtain the catalyst. The binder may be zeolite, silicon carbide, silica, silica-alumina, silicates, aluminates and borates and the like.

The catalyst according to the invention needs to be reduced before use just as the ordinary copper-containing catalysts do. The reduction medium may be pure hydrogen gas or hydrogen-containing nitrogen gas. The reduction of the catalyst is carried out by elevating the temperature of the reduction medium to a given level and maintaining the temperature constant for a certain period of time, then the temperature is lowered to the reaction temperature and the feedstock may be fed in to start the catalystic reaction. In order to avoid an undue temperature rise or even a runaway temperature to overburn the catalyst during the reduction process affecting the catalytic performance of the catalyst, the reduction medium is preferably a nitrogen gas containing 5 vol % of hydrogen, and the rate of rise of temperature should be strictly controlled so that the temperature rise in the catalyst bed is less than 20° C., while the reduction temperature is at 200–250° C., preferably 210–230° C.

The catalyst according to the invention is suitable for use in various chemical processes, for example, the process of methanol synthesis from a mixed gas of CO, $CO_2$ and $H_2$, and the low temperature shift process, which need the catalytic action of a copper-containing catalyst, such as a copper/zinc oxide or a copper/zinc oxide/alumina catalyst, and is especially suitable for hydrogenation of aldehydes and/or ketones in gas phase and dehydrogenation of alcohols, for example, the hydrogenation of linear or branched and saturated or unsaturated aldehydes and/or ketones having 2–22 carbon atoms, in particular the mixture of aldehydes derived from an oxo synthesis or a part thereof such as n-butanal, iso-butanal or 2-ethylhexenal, into the corresponding alchols; or the dehydrogenation of alcohols having 2–22 carbon atoms such as iso-propanol or sec-butanol into the corresponding ketones such as acetone or methyl ethyl acetone.

The above chemical processes using the catalyst of the present invention can be carried out in a conventional way of the art, for example, those described in U.S. Pat. Nos. 4,279,781 and 4,876,402 and in Examples 4–6 herein.

Compared with the prior arts, the catalyst according to the present invention and the preparation process thereof do not involve in washing off sodium with pure water, so the preparation process is simplified and rid of the problems of environmental protection and waste water treatment as that arisen in the prior art; particularly, the preparation process of the catalyst according to the present invention has good repeatability since the intermediate insoluble salt coprecipitates of the process are uniform in structure; and moreover since copper and zinc compound are precipitated simultaneously during the coprecipitation process to form crystal precipitate in uniform and superfine particles, the catalyst obtained therefrom has comparatively large specific surface area, pore volume, pore diameter and high bulk specific density, therefore the catalyst of the present invention is superior to that prepared by the conventional process using sodium carbonate in activity, selectivity and stability. Besides, the costs for the production and starting materials of the catalyst according to the invention are reduced.

EXAMPLES

Figure 1:
FIG. 1 shows the lattice image (X175000) of a comparative catalyst, measured by the transmission electron microscopy (TEM).

The present invention is further illustrated in detail with reference to the following examples which are provided for purposes of illustration and shall not be construed as limiting the present invention.

Comparative Example 1

The $CuO/ZnO/Al_2O_3$ catalyst of this comparative example was prepared according to the process described in U.S. Pat. No. 5,302,569.

435.6 g copper nitrate, 261.5 g zinc nitrate and 89.5 g aluminum nitrate were dissolved in 1800 ml deionized water to form a mixed-salt solution, and heated to 80° C.; 375.0 g sodium carbonate was dissolved in 3000 ml deionized water, and heated to 80° C.

800 ml deionized water was added into a precipitation tank and heated to 80° C. The two solutions mentioned above were fed in separate but simultaneous flows into the precipitation tank in 20 minutes with stirring, with the two flows being well matched to ensure the pH value of the solution in the tank being in a range of 7.5–7.8 and the temperature maintained constant at 80° C.

After the precipitation completed, the resulting suspension was stirred continuously for 2 minutes, then filtered, and washed with 12 liters of deionized water at 60–65° C. for 2 hours, the resulting filter cake was then dried at 110° C. for 8 hours and calcined at 400° C. for 4 hours, then an appropriate amount of graphite was added and mixed homogeneously, and pressed and moulded into a shape to obtain the $CuO/ZnO/Al_2O_3$ catalyst.

The obtained catalyst has a BET specific surface area of 120.1 m²/g, a pore volume of 0.45 ml/g and an average pore diameter of $150 \times 10^{-10}$ m, and has a crystallite distribution wherein the crystallites having a diameter of less than 1.0 nm account for 10%, those of 1.0–2.0 nm account for 50%, and those of more than 2.0 nm account for 40%.

Example 1

The $CuO/ZnO/Al_2O_3$ catalyst of this example was prepared with the same ratio of metals as that of the Comparative Example 1.

435.6 g copper nitrate, 261.5 g zinc nitrate and 89.5 g aluminum nitrate were formulated into 2000 ml mixed-salt solution; and 416.0 g malonic acid was formulated into 2000 ml precipitant solution. The solutions were added separately into two parallel elevated tanks and heated simultaneously to 25° C.

The two solutions were fed in separate but simultaneous flows into a precipitation tank at a lower position in 20 minutes with vigorous stirring while maintaining the temperature with a water bath, then aged with weak stirring for 5 minutes, and then filtered. The obtained filter cake was dried at 110° C. for 8 hours, and calcined at 360° C. for 4 hours, then an appropriate amount of graphite was added and mixed homogeneously, and pressed and moulded into shape to obtain the $Cu/ZnO/Al_2O_3$ catalyst.

The catalyst has a BET specific surface area of 136.2 m²/g, a pore volume of 0.58 ml/g, and an average pore diameter of $171 \times 10^{-10}$ m, and has a crystallite distribution wherein the crystallites having a diameter of less than 1.0 nm account for 10%, those of 1.0–2.0 nm account for 80%, and those of more than 2.0 nm account for 10%.

Comparable Example 2

The CuO/ZnO catalyst of this comparative example was prepared according to the process described in U.S. Pat. No. 4,876,402.

1600 ml of a solution containing 41.7 g copper (added as copper nitrate) and 85.8 g zinc (added as zinc nitrate) was heated to 43° C., and sprayed to 1300 ml of 15.7% sodium carbonate solution with mechanical stirring while keeping at a constant temperature of 60° C. to provide a final precipitate mixture having a pH value of about 7.9–8.5. After precipitation, the copper/zinc subcarbonates were filtered, then pulped and washed with deionized water at 37.8–48.8° C. The pulping and washing were repeated for 4 times to remove sodium salt from the filter cake to such a degree that the sodium content of the mixed oxides after calcination was reduced to 0.10–0.15%. The filter cake was dried at 110° C. for 8 hours, and calcined at 400° C. for 4 hours, then an appropriate amount of graphite was added and mixed homogeneously, then pressed and moulded into shape to obtain the catalyst.

The catalyst has a BET specific surface area of 36.5 m²/g, a pore volume of 0.16 ml/g, and an average pore diameter of $175 \times 10^{-10}$ m, and has a crystallite distribution wherein the crystallites having a diameter of less than 1.0 nm account for 5%, those of 1.0–2.0 nm account for 50%, and those of more than 2.0 nm account for 45%. See FIG. 1 showing the lattice image of the catalyst, which was photographed (X175000) using an EM420 type transmission electron microscope (available from the Philip Company, the Netherlands).

Example 2

The CuO/ZnO catalyst of this example was prepared with the same ratio of metals as that of Comparative Example 2.

96.5 g copper nitrate, 235.0 g zinc nitrate were formulated into 2000 ml mixed-salt solution, and 170.0 g oxalic acid was formulated into 3000 ml precipitant solution which was then adjusted to a pH value of 5.0. The two solutions were then fed separately into two parallel elevated tanks and heated to 45° C. respectively, and were separately but simultaneously added into a precipitation tank at a lower position in 20 minutes with vigorous stirring while maintaining the temperature with a water bath, then aged with weak stirring for 0.5 hour, and filtered and air-dried; the obtained filter cake was dried further at 110° C. for 8 hours, and calcined at 360 ° C. for 4 hours, then the obtained mixed oxides were mixed homogeneously with an appropriate amount of graphite, pressed and moulded into shape to obtain the catalyst.

The catalyst has a BET specific surface area of 41.4 m²/g, a pore volume of 0.20 ml/g, and an average pore diameter of $191 \times 10^{-10}$ m, and has a uniform crystallite distribution wherein the crystallites having a diameter of less than 1.0 nm account for 5%, those of 1.0–2.0 nm account for 92%, and those of more than 2.0 nm account for 3%. See FIG. 2 showing the lattice image of the catalyst, photographed (X175000) using the EM420 type transmission electron microscope.

Figure 2:
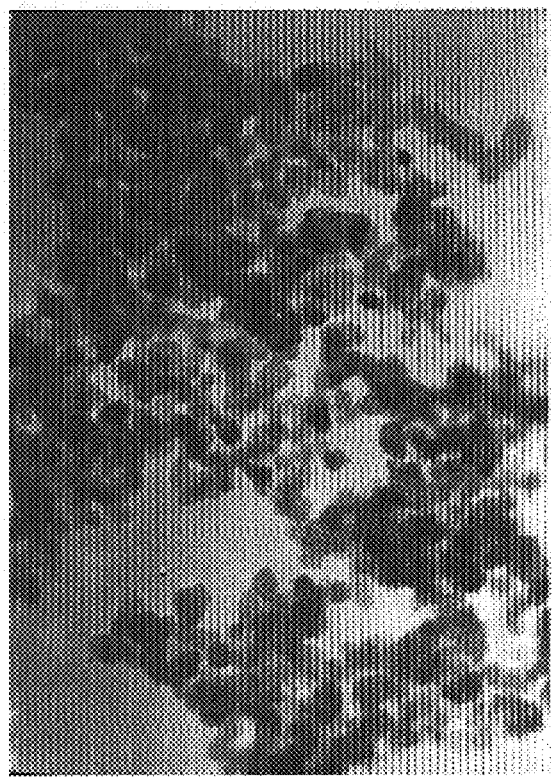
FIG. 2 shows the lattice image (X175000) of the present invention, measured by the transmission electron microscopy (TEM)

It can be seen from the comparison between the results of FIGS. 1 and 2 that the copper-containing catalyst of the prior art has notably different crystallite sizes of which the large crystallites are 10 times the size of the smaller and the crystal shapes are irregular, but in contrast to the comparative catalyst, the catalyst of the present invention has a uniform crystallite distribution wherein the crystallites having a diameter of 1.0–2.0 nm account for about 90% and is in regular spherical shape.

Example 3

The catalyst of this example comprises the same essential components CuO and ZnO in the same ratio as that of a commercial catalyst which contains CuO of 50% and ZnO of 50% based on the weight of the catalyst (hereinafter referred to as the comparative catalyst R1), and which was obtained by the prior art process in which sodium carbonate was used as coprecipitant.

151.8 g copper nitrate and 182.7 g zinc nitrate were formulated into 1000 ml mixed-salt solution and the resulting solution was placed in a precipitation tank at a lower position. 172.0 g ammonium oxalate was formulated into 1500 ml precipitant solution having a pH value of 7.0, and the resulting solution was then placed in an elevated tank. The two solutions were heated to 60° C. simultaneously, and then the ammonium oxalate solution was added in 15 minutes to the mixed-salt solution with vigorous stirring. The resultant precipitate was then worked-up, dried, calcined and moulded into shape by the same steps and conditions mentioned in Example 2 to obtain the catalyst.

This catalyst has a BET specific surface area of 29.1 m$^2$/g, a pore volume of 0.16 ml/g, and an average pore diameter of 222×10$^{-10}$ m, and has a uniform crystallite distribution wherein the crystallites having a diameter of less than 1.0 nm account for 5%, those of 1.0–2.0 nm account for 93%, and those of more than 2.0 nm account for 2%; while the comparative catalyst R1 has a BET specific surface area of 22.5 m$^2$/g, a pore volume of 0.11 ml/g, and an average pore diameter of 201×10$^{-10}$ m, and has a crystallite distribution wherein the crystallites having a diameter of less than 1.0 nm account for 5%, those of 1.0–2.0 nm account for 50%, and those of more than 2.0 nm account for 45%.

Example 4

In this example, the catalysts from the Comparative Example 1 and from Example 1 were tested comparatively for their catalytic performances with respect to the synthesis of methanol from a mixed gas of CO, CO$_2$ and H$_2$.

The evaluation was carried out in an apparatus with a fixed bed microreactor filled with 4 ml of a catalyst to be tested having a particle size of 0.45–0.90 mm. Firstly, a mixed gas of H$_2$/Ar (with a volume ratio of 5:95) was introduced at a flow rate of 40 ml/min under a pressure of 0.50 MPa into the apparatus, which was then heated from room temperature to 220° C. in 4 hours. After the reduction reaction was carried out at the constant temperature for 4 hours, the temperature was reduced to 110° C., and the mixed gas being introduced was substituted with a mixture of CO, CO$_2$ and H$_2$ (with a volume ratio of 3.7:2.3:94). The pressure was set at 5.0 MPa and the space velocity at 10,000 h$^{-1}$, and then the temperature was raised at a rate of 20° C./h to 240° C. and the reaction was carried out. The flow rate of the mixed gas was controlled with a mass flow gauge. The reaction products were analyzed by an on-line gas chromatography using a thermal conductivity cell as detector and two chromatographic column, in which a column Porapak-Q of 2 meters in length was used for the analysis of CH$_3$OH, dimethyl ether, higher alcohols and other hydrocarbon products, and a column TDX-01 of 2 meters in length for the analysis of CO, CO$_2$ and CH$_4$. The relative content of each component in the product mixture was calculated via the normalized area. The results are shown in Table 1.

TABLE 1

| Comparison between the performances of the catalysts with respect to the synthesis of methanol from a mixed gas of CO, CO$_2$ and H$_2$ | | |
|---|---|---|
| Catalyst from | Liquid yield* (%) | Relative activity** |
| Comp. Ex. No. 1 | 0.303 | 1.00 |
| Ex. No. 1 | 0.480 | 1.58 |

*Liquid yield: volumn of the formed methanol/volumn of catalyst/h;
**Relative activity: given the activity of the comparative catalyst as 1.00.

Example 5

In this example, the catalysts from the Comparative Example 2 and from Example 2 were tested comparatively for their catalytic performances with respect to the hydrogenation of n-butanal.

The evaluation was carried out in an apparatus with a fixed bed microreactor filled with 4 ml of a catalyst to be tested having particle size of 0.45–0.90 mm. Firstly, hydrogen was introduced (with a volume ratio of H$_2$/catalyst of 500:1) under a hydrogen pressure of 0.40 MPa into the apparatus which was heated from room temperature to 220° C. in 4 hours, and then the catalyst was reduced at the constant temperature for 1 hour. After the temperature dropped to 150° C., n-butanal was introduced at a space velocity of the n-butanal of 0.5 h$^{-1}$ and a volume ratio of hydrogen to butanal of 6000:1. The product mixture was analyzed by a gas chromatography using helium as carrier gas, polyhydroxyethyl nonyl phenyl ether as stationary liquid and Chromosrb W as stationary phase, with the thermal conductivity cell as the detector, and the relative content of each component in the product mixture was calculated via the normalized area. The results are shown in Table 2.

TABLE 2

| Comparison between the performances of the catalysts with respect to the hydrogenation of n-butanal | | |
|---|---|---|
| The catalyst from | Comparative Example 2 | Example 2 |
| Conversion (wt %) | 99.2 | 99.7 |
| Selectivity to butanol (%) | 98.8 | 99.5 |

Example 6

In this example, the catalysts from Example 3 and a commercial Cu/ZnO catalyst (the comparative catalyst R1) were tested comparatively for their catalytic performances with respect to the dehydrogenation of sec-butanol. The evaluation was conducted in a small-scale fixed bed reactor using 20 ml of a catalyst to be tested having a particle size of 0.45–1.8 mm. After the reactor was heated from room temperature to 150° C. in 3 hours, sec-butanol was fed at a space velocity of 2.0 h$^{-1}$ under a pressure of 0.2 MPa, to reduce the catalyst at the constant temperature for 8 hours, then the temperature was raised at a rate of 50° C./hour to 260° C., and then stabilized for 8 hours. The reaction product was sampled for analysis by a gas chromatography using hydrogen as carrier gas and polymer porous microsphere GDX-103 as stationary phase, with the thermal conductivity cell as the detector, and the relative content of each component in the product mixture was calculated via the normalized area. The results are shown in Table 3.

TABLE 3

Comparison between the performances of the catalysts with respect to the dehydrogenation of sec-butanal

| The catalyst from | The comparative catalyst R1 | Example 3 |
|---|---|---|
| Conversion (wt %) | 75.2 | 80.1 |
| Selectivity to methyl ethyl acetone (%) | 96.1 | 98.0 |

What is claimed is:

1. A copper-containing catalyst having a uniform crystallite distribution wherein crystallites having a diameter of less than 1.0 nm account for 0–20%, those of 1.0–2.0 nm account for 70–99%, and those of more than 2.0 nm account for 0–20%.

2. A copper-containing catalyst according to claim 1, wherein said catalyst does not contain sodium.

3. A copper-containing catalyst according to claim 1 or 2, wherein said catalyst has such a uniform crystallite distribution that the crystallites having a diameter of less than 1.0 nm account for 0–15%, those of 1.0–2.0 nm account for 75–98%, and those of more than 2.0 nm account for 0–15%.

4. A copper-containing catalyst according to claim 1 or 2, wherein said catalyst has such a uniform crystallite distribution that the crystallites having a diameter of less than 1.0 nm account for 0–10%, those of 1.0–2.0 nm account for 80–95%, and those of more than 2.0 nm account for 0–10%.

5. A copper-containing catalyst according to claim 1, wherein said catalyst has a specific surface area of 30–50 $m^2/g$, a pore volume of 0.10–0.25 ml/g, and an average pore diameter of 10–25 nm.

6. A copper-containing catalyst according to claim 1 or claim 5, wherein said catalyst comprises copper oxide of 30–70 wt %, zinc oxide of 30–70 wt % and alumina of 0–30 wt %.

7. A copper-containing catalyst according to claim 6, wherein said catalyst comprises copper oxide of 33–50 wt %, zinc oxide of 50–65 wt % and alumina of 10–25 wt %.

8. A copper-containing catalyst according to claim 4, wherein said crystallites having a diameter of less than 1.0 nm account for 2–5%.

9. A copper-containing catalyst according to claim 4, wherein said crystallites having a diameter of 1.0–2.0 nm account for 80–93%.

10. A copper-containing catalyst according to claim 4, wherein said crystallites having a diameter of more than 2.0 nm account for 2–5%.

11. A copper-containing catalyst according to claim 5, wherein said catalyst has a specific surface area of 35–45 $m^2/g$.

12. A copper-containing catalyst according to claim 5, wherein said catalyst has a pore volume of 0.15–0.20 ml/g.

13. A copper-containing catalyst according to claim 5, wherein said catalyst has an average pore diameter of 15–20 nm.

14. A process for preparing a copper-containing catalyst by a co-precipitation method, comprising the steps of mixing a working salt solution containing soluble metal salts for co-precipitation and a solution containing organic acid(s) and/or ammonium salt(s) thereof as co-precipitant, and co-precipitating out a mixture of insoluble metal salts containing copper, wherein said organic acid(s) and/or ammonium salt(s) thereof used as co-precipitant is selected from the group consisting of oxalic acid, malonic acid, succinic acid, and glutaric acid and ammonium salts thereof, and said co-precipitant solution used in the step of co-precipitation has a concentration of 0.10–0.80 M and a pH value of 3.0–7.0.

15. A process for preparing a copper-containing catalyst according to claim 14, wherein said catalyst comprises copper oxide of 30–70 wt %, zinc oxide of 30–70 wt % and alumina of 0–30 wt %.

16. A process for preparing a copper-containing catalyst according to claim 15, wherein said catalyst comprises copper oxide of 33–50 wt %, zinc oxide of 50–65 wt % and alumina of 10–25%.

17. A process for preparing a copper-containing catalyst according to claim 14, wherein said organic acid(s) and/or ammonium salt(s) thereof used as co-precipitant is selected from the group consisting of malonic acid, oxalic acid and ammonium salts thereof.

18. A process for preparing a copper-containing catalyst according to claim 14, wherein said organic acid(s) and/or ammonium salt(s) thereof used as co-precipitant is succinic acid and/or ammonium salt thereof.

19. A process for preparing a copper-containing catalyst according to claim 14, wherein the working salt solution used in the step of co-precipitation has a concentration of 0.10–0.80 M.

20. A process for preparing a copper-containing catalyst according to claim 14, wherein said co-precipitation step is carried out at a temperature of 15–70° C.

21. A process for preparing a copper-containing catalyst according to claim 14, wherein the amount of said co-precipitant used in the co-precipitation step exceeds by 5–20 wt % over the stoichiometrical amount of metal ions completely precipitated from the working salt solution.

22. A process for preparing a copper-containing catalyst according to claim 14, wherein said working salt solution used in the co-precipitation step has a concentration of 0.3–0.5 M.

23. A process for preparing a copper-containing catalyst according to claim 14, wherein said co-precipitant solution used in the co-precipitation step has a concentration of 0.30–0.50 M and pH value of 4.0–6.0.

24. A process for preparing a copper-containing catalyst according to claim 14, wherein said co-precipitation step is carried out at a temperature of 25–45° C.

25. A process for preparing a copper-containing catalyst according to claim 14, wherein the amount of said co-precipitant used in the co-precipitation step exceeds by 10–15 wt % over the stoichiometrical amount of metal ions completely precipitated from the working salt solution.

26. A process for preparing a copper-containing catalyst according to claim 14, wherein during the co-precipitation, a working salt solution and the co-precipitant solution are separately added into two parallel elevated tanks and heated, and then separately but simultaneously added into a precipitation tank at a lower position with heat preservation and stirring.

* * * * *

UNITED STATES PATENT AND TRADEMARK OFFICE
CERTIFICATE OF CORRECTION

PATENT NO. : 6,689,713 B1
DATED : February 10, 2003
INVENTOR(S) : Leping Zhao et al.

It is certified that error appears in the above-identified patent and that said Letters Patent is hereby corrected as shown below:

<u>Title page,</u>
Item [75], Inventors, the first inventor's name should read -- Leping Zhao -- rather than "Leiping Zhao".

Signed and Sealed this

Sixth Day of April, 2004

JON W. DUDAS
*Acting Director of the United States Patent and Trademark Office*